United States Patent [19]

Amir et al.

[11] Patent Number: 4,929,845

[45] Date of Patent: May 29, 1990

[54] METHOD AND APPARATUS FOR INSPECTION OF SUBSTRATES

[75] Inventors: Israel Amir; Frank P. Higgins, both of Ewing, N.J.

[73] Assignee: AT&T Bell Laboratories, Murray Hill, N.J.

[21] Appl. No.: 316,004

[22] Filed: Feb. 27, 1989

[51] Int. Cl.$^5$ ............................................. G01N 21/86
[52] U.S. Cl. ...................................... 250/561; 356/394
[58] Field of Search ............... 250/560, 561, 562, 563, 250/571, 572; 356/394, 398; 358/101, 106, 107; 382/62, 65, 48

[56] References Cited

U.S. PATENT DOCUMENTS

| | | | |
|---|---|---|---|
| 3,069,654 | 12/1962 | Hough | 340/146.3 |
| 3,695,771 | 10/1972 | Bardos | 356/210 |
| 3,794,427 | 2/1974 | Shibata et al. | 356/120 |
| 3,796,500 | 3/1974 | Obser | 356/237 |
| 3,877,814 | 4/1975 | Hess et al. | 356/120 |
| 3,962,681 | 6/1976 | Requa et al. | 340/146.3 H |
| 4,131,804 | 12/1978 | Sick et al. | 250/566 |
| 4,240,750 | 12/1980 | Kurtz et al. | 356/394 |
| 4,295,198 | 10/1981 | Copeland | 364/515 |
| 4,379,308 | 4/1983 | Kosmowski et al. | 358/106 |
| 4,473,842 | 9/1984 | Suzuki et al. | 358/107 |
| 4,545,070 | 10/1985 | Miyagawa et al. | 382/48 |
| 4,569,079 | 2/1986 | Yoshida | 358/1 |
| 4,570,181 | 2/1986 | Yamamura | 358/160 |
| 4,578,810 | 3/1986 | MacFarlane et al. | 382/8 |
| 4,677,303 | 6/1987 | Erdman | 250/561 |
| 4,803,871 | 2/1989 | Harada et al. | 356/394 |

OTHER PUBLICATIONS

W. M. Hastie, *Circuits Manufacturing*, Feb. 1985, pp. 72-90, "Machine Vision Eyes Loaded Boards."
S. W. Fields, *Electronics*, Aug. 25, 1983, pp. 163-164, "System Inspects Board in 2.4 Seconds."
D. Marro, *Research & Development*, May, 1985, pp. 114-116, "Does Your PCB Assembly Line Have Eyes?"

Primary Examiner—David C. Nelms
Attorney, Agent, or Firm—Robert B. Levy

[57] ABSTRACT

Inspection of a circuit board (10) to detect missing and misaligned active and passive surface-mounted components (12) and (14), respectively, is accomplished by first illuminating the board with top light to enhance the image of the passive components. The circuit board is then displaced, relative to a linescan camera (28) trained on the board, so that the camera captures the image of successive strips of surface area running across the board perpendicular to its direction of movement. The images captured by the camera (28) are stored and thereafter processed by an image-processing system (33) to determine whether any passive component is missing or misaligned. The circuit board is then illuminated with side light to enhance the image of the active components. The circuit board is again displaced relative to the linescan camera so the camera captures the image of successive strips of surface area on the board. The captured images are stored and then processed by the image-processing system to detect whether any of the active surface-mounted components are missing or misaligned.

7 Claims, 2 Drawing Sheets

METHOD AND APPARATUS FOR INSPECTION OF SUBSTRATES

This invention relates to a technique for inspecting a substrate, such as a circuit board, to detect missing and misaligned components.

BACKGROUND OF THE INVENTION

Presently, circuit boards containing "surface-mounted" components, i.e., components which have conductive members (leads or pads) solder-bonded to corresponding metallized areas on the surface of the board, are fabricated in the following manner. First, a volume of solder paste is printed on the surface of the circuit board, or alternatively, a quantity of solder is applied to each conductive member of each component. Next, components are placed on the circuit board so that each conductive member on each component is in registration with a corresponding metallized area on the board surface. After placement, the component is adhered to the circuit board, either by the tackiness of the solder paste, or in the absence of any paste, by a conventional adhesive. Finally, the circuit board is heated, causing the solder paste on the board, or alternatively, the solder applied to the conductive member of each component, to reflow, thus creating a bond between the component and the circuit board.

Prior to the heating of the circuit board to reflow the solder or solder paste, it is useful to inspect the board to ensure that there are no missing or misaligned components. Repair of a circuit board having misaligned or missing surface-mounted components is far easier before the components are soldered in place than afterwards. However, in order for such "pre-solder" inspection to be useful, such an inspection must be carried out rapidly and with high accuracy.

Now-allowed U.S. patent application Ser. No. 111,954, filed in the name of I. Amir et al. on Oct. 23, 1987, and assigned to AT&T, discloses a system for inspecting a circuit board to detect missing and misaligned components. The inspection system disclosed in that application (incorporated by reference herein) is capable of reliably detecting missing or misaligned "passive" surface-mounted components (i.e., resistors and capacitors). However, the aforementioned inspection system does not reliably detect whether any active component, such as a plastic leaded chip carrier (plcc), soldered-on integrated circuit (soic), or soldered-on transistor (sot), is missing or misaligned.

Thus, there is a need for a technique for inspecting a circuit board to detect missing and misaligned passive and active surface-mounted components.

SUMMARY OF THE INVENTION

Briefly, in accordance with the invention, a method is provided for inspecting a substrate, such as a circuit board, to detect missing or misaligned active, as well as passive surface-mounted components. Initially, the circuit board is illuminated with "top light" by directing light towards the board so it strikes the board surface substantially normal to its plane. A light-sensing device, typically a linescan camera, has its optical axis substantially normal to plane of the surface of the circuit board to capture the image of a thin strip of surface area running across the board. A relative motion is imparted between the linescan camera and the circuit board so the camera captures the image of successive strips of surface area on the board. The image of each successive strip of area on the circuit board surface is stored for subsequent processing to detect whether there are any missing or misaligned passive components. Once the image of each successive strip of surface area has been stored, then the circuit board is illuminated with "side light," by directing light at the surface of the board at a grazing angle. A relative motion is then imparted between the board and the linescan camera in the opposite direction as before so that the camera can again capture the image of successive strips of surface area on the board. The images are then stored for processing to detect whether there are any missing or misaligned active components.

When the surface of the circuit board is illustrated with top light, the leads on the passive components, as well as fiducial marks on the board, become more visible to the linescan camera, allowing for more accurate detection of missing or misaligned passive components. When the board is illuminated with side light, the leads on the active devices are more visible to the linescan camera, thus allowing missing and misaligned active components to be more readily detected.

DETAILED DESCRIPTION

Figure 1:
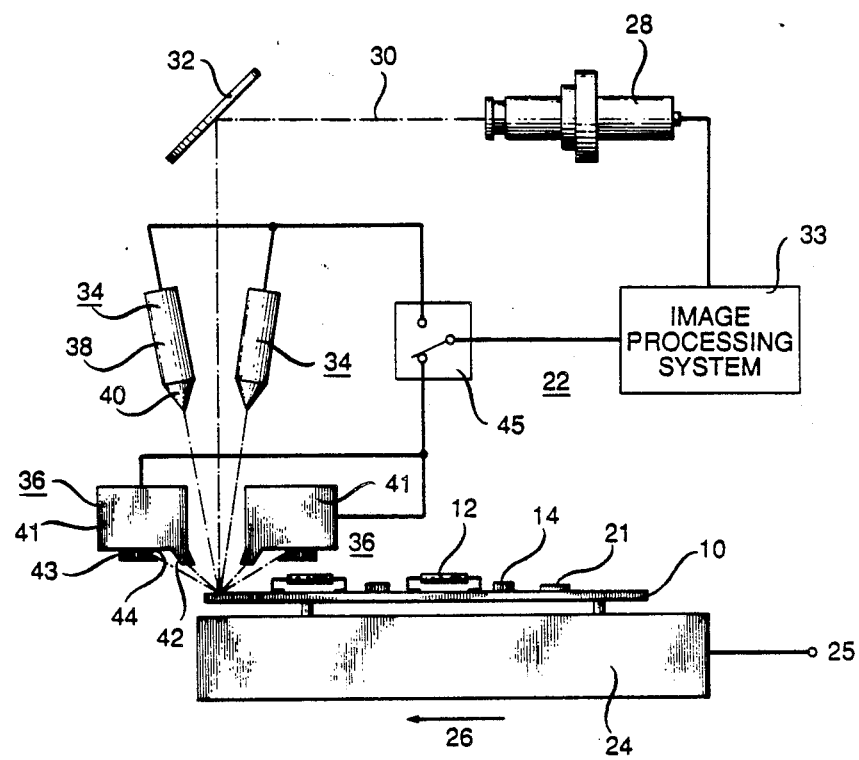
FIG. 1 is a schematic view of a circuit board inspection system, in accordance with the invention, depicting operation of the system in a first mode.
Figure 2:
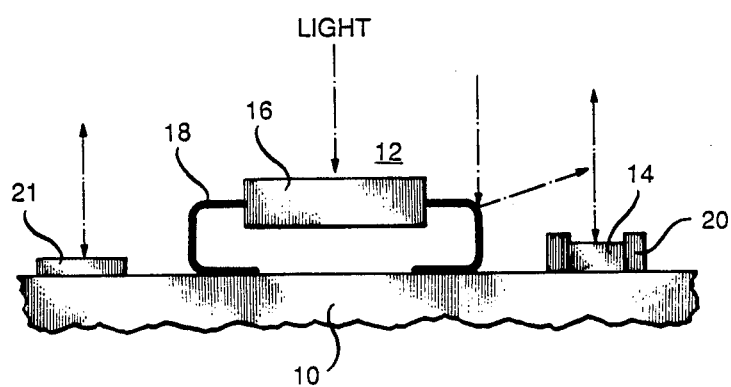
FIG. 2 is an enlarged side view of a passive and an active surface-mounted component on the circuit board of FIG. 1.

FIG. 1 shows a conventional printed circuit board 10 which is populated with both active and passive surface-mounted components 12 and 14. As illustrated in FIG. 2, which is an enlarged side view of the circuit board 10, each active component 12, typically, a plcc, soic, or an sot, is comprised of a pismatic body 16 having a plurality of light-reflective metal leads 18 extending from one or more of its sides. In an exemplary embodiment, the component 12 is depicted as a plcc whose leads 18 are "J-leaded" and are tucked substantially underneath the body 18. The passive component 14, typically a resistor or capacitor, is generally short and planar in shape. At each end of the component 14 is a metallized pad 20 which serves as one of the component's two leads.

Referring to FIGS. 1 and 2, in addition to the components 12 and 14, the circuit board 10 also carries a plurality of fiducial marks 21, each formed of a distinctive metallized area on the surface of the board. The fiducials 21 are situated at known locations on the surface of the circuit board 10. Thus, the position of each of the components 12 and 14 can be determined by knowing the distance from the fiducials 21.

When fabricating the circuit board 10, it is desirable to detect whether any of the components 12 and 14 are missing or misaligned prior to their being soldered in place. Repair of the circuit board 10 to correct these types of defects is more easily accomplisned prior to soldering of the components 12 and 14 in place than afterwards. In FIG. 1, there is shown a schematic view of a system 22, in accordance with the invention, for inspecting the circuit board 10 to detect whether any of the active and passive components 12 and 14 are missing or misaligned. The inspection system 22 is comprised of a support 24 which seats the circuit board 10. Suitable clamping means (not shown) are provided to hold the circuit board 10 in place on the support. A motor 25 serves to displace the support 24 in opposite directions along an axis 26.

A linescan camera 28 is located above the circuit board 10 for capturing its image. The camera 28 is of a well-known design and includes a plurality of charge-coupled devices (ccd's) (not shown) arranged in a 1×N (where N is the number of ccd's) linear array lying along a line normal to the plane of the drawing. Each of the ccd's within the camera 28 serves to capture the image of a small picture element (pixel) so that the array of ccd's collectively captures the image of a thin strip of area whose longitudinal axis is normal to the plane of the drawing.

In the embodiment shown in FIG. 1, the camera 28 is positioned such that its optical axis 30 (i.e., the axis along which light is detected by the ccd's in the camera) is parallel to the plane of the circuit board. The optical axis 30 of the camera 28 is reflected by a mirror 32 downwardly onto the surface of the circuit board 10 normal to the board surface. With the optical axis 30 of the camera 28 reflected by mirror 30 onto the surface of the circuit board 10, the camera will capture the image of a thin strip of surface area running across the board surface normal to the plane of the drawing. When the support is displaced along the axis 26, the camera 28, which remains fixed, will capture the image of successive strips of area on the surface of the circuit board 10. Rather than use the mirror 32 to reflect the optical axis 30 of the camera 28 onto the circuit board 10, the camera could be trained directly onto the board.

The camera 28 supplies an analog signal, which varies in intensity in accordance with the captured image of the circuit board 10, to an image-processing system 33. The image-processing system 33 is identical in configuration to the image-processing system described in the aforementioned, now-allowed U.S. patent application, serial no. 111,954. A complete description of the image-processing system 33 may be had by reference to that now-allowed application (incorporated by reference herein) and for purposes of brevity, the structural details of the image-processing system have been omitted.

In operation, the image-processing system 33 processes the output signal of the camera 28 by first converting the signal into a stream of digital signals, each varying in accordance with the intensity of the pixel captured by a corresponding one of the ccd's in the camera 28. The digital signals are winnowed such that only those signals representing a corresponding one of the pixels within each region of interest on the board 10 (i.e., the regions where any part of any of the components 12 and 14 and the fiducials 21 are located) are stored. The stored signals are then processed to detect the position of the fiducials 21 and then to determine whether the components 12 and 14 are in fact present and are positioned properly (with respect to the fiducials).

In order for the image-processing system 33 to detect the presence and proper position of the components 12 and 14 on the circuit board 10, the image of the components and the image of the fiducials 21 captured by the camera 28 must be sharp. For the most part, the only features on the components 12 and 14 which reflect much light and thus appear sharp are the component leads 18 and 20, respectively. Thus, the best way to detect the presence and proper positioning of the components 12 and 14 is to detect whether their leads 18 and 20, respectively, are present and are properly positioned.

Referring to FIG. 2, we found that when the circuit board 10 was illuminated with top light, (i.e., light directed at the board surface normal to its plane), the light striking each lead 20 on the component 14 and the light striking each fiducial 21 was reflected upwardly therefrom substantially normal to the plane of the board surface. Since the camera 28 of FIG. 1 has its optical axis 30 reflected by the mirror 30 downwardly onto the surface of the circuit board 10 substantially normal thereto, the leads 20 and the fiducials 21 were quite visible to the camera when the board was illuminated with top light.

However, we found that when the circuit board 10 was illuminated with top light, the light striking the leads 18 on the component 12 tended to be reflected at an angle of less than 90° with respect to the surface of the circuit board 10. Hence, the light striking the leads 18 was reflected away from the camera 28, causing the leads to appear very dull. Conversely, when the circuit board 10 was illuminated with side light by directing light at the board surface at a grazing angle, light was reflected into the camera 28 by the leads 18 of the component 20, causing them to appear bright. However, little light was reflected into the camera 28 from the leads 20 on the component 14 and from the fiducials 21.

To ensure proper lighting of the circuit board 10, the inspection system 22 of FIG. 1 incorporates two pairs of light sources 34 and 36. The light source pairs 34 and 36 are supported above the circuit board 10 by a bracket (not shown) so that each light source of each pair is situated on a separate one of the sides of the downwardly reflected portion of the optical axis 30 of the camera 28. The light source pairs 34 and 36 illuminate the circuit board 10 and, in particular, the strip of area thereon imaged by the camera 28, with top light and with side light, respectively.

In practice, each pair of light sources 34 comprises a bar 38 which mounts a plurality of light guide fibers 40 in spaced relationship along an axis normal to the plane of the drawing. The fibers 40 are each supplied at a first end with light from a lamp (not shown), and each has its opposite end directed at the circuit board 10 for radiating light onto the board surface generally within the strip of area imaged by the camera 28. Typically, the angle between the beams of light leaving the end of each fiber 40, and the downwardly directed portion of the optical axis 30, is very small (<5°) and has been is exaggerated in the drawing.

The light sources 36 are each comprised of a bar 41 which carries a plurality of triangular mirrors 42, each typically formed of a three-sided metal prism reflector, and spaced along an axis normal to the plane of the figure. Each mirror 42 is secured to the bar 41 such that two of its sides slope downwardly, in opposite directions towards the circuit board 10, while the third side is parallel to the board surface. Each of the two downwardly sloping sides of each mirror 42 also slopes laterally inwardly, towards the downwardly reflected portion of the optical axis 30 of the camera 28.

When light is directed at each mirror 42 from a lamp (not shown) via a fiber (not shown), the mirror splits the light into two beams, each directed at the surface of the circuit board 10 at a grazing angle, generally along an axis normal to the plane of the figure. The two beams reflected by each mirror 42 onto the surface of the circuit board 10 each overlap with the one of the beams reflected from each adjacent mirror so that each light source illuminates a strip of area running across the surface of the circuit board 10 normal to the axis 26.

In addition to the mirrors 42, each light source 36 also includes an elongated mirror 43 secured to the bottom of the bar 41 in spaced relationship with the mirrors 42 so as to extend along an axis normal to the plane of the drawing. The mirror has a light-reflective edge 44 which slopes at a downwardly inclined angle towards the circuit board 10. When light is directed at the lightreflective edge 44 from a lamp (not shown) through a set of fibers (not shown), the light is reflected towards the circuit board at a grazing angle in a direction generally parallel to the axis 26.

A more complete description of each light source 36 may be found in co-pending application, serial no. (Amir-4), filed in the name of I. Amir, herein incorporated by reference.

The light source pairs 34 and 36 are selectively operated by the image-processing system 33 through a switch 45, so that only one pair of sources is operative at one time. As seen in FIG. 1, the pair of sources 34 is operative, while the pair of sources 36 is not. In FIG. 2, the opposite condition is depicted; the pair of light sources 36 is operative while the pair of light sources 34 is not. When inspecting the circuit board 10 for missing and misaligned active components 12, it is undesirable to illuminate the circuit board 10 with both side and top light at the same time because the top lighting will "wash out," that is, distort the image of the leads 18. It is, however, possible to detect the leads 20 and the fiducials 21 when the board is illuminated with both top and side light. However, for simplicity purposes, only one pair of light sources 34 and 36 is However, for simplicity purposes, only one pair of light sources 34 and 36 is rendered operative at one time.

In operation, the circuit board 10 is first clamped to the support 24, and the switch 45 is actuated by the image processor 33 to actuate the light source pair 34. The support 24 is then displaced along the axis 26, so that the camera 28 captures the image of successive strips of surface area running across the circuit board 10. The output signal of the camera 28 is processed in the manner described earlier so that only selected digital signals are stored, the stored signals representing the images of those regions of interest on the circuit board 10 containing the leads 20 of the components 14 and the fiducials 21. The stored digital signals are then processed to determine the location of the leads 20 from the fiducials 21. Then, the actual location of the leads 18 is compared with the expected lead position to determine if any of the components 14 are missing or misaligned.

Figure 3:
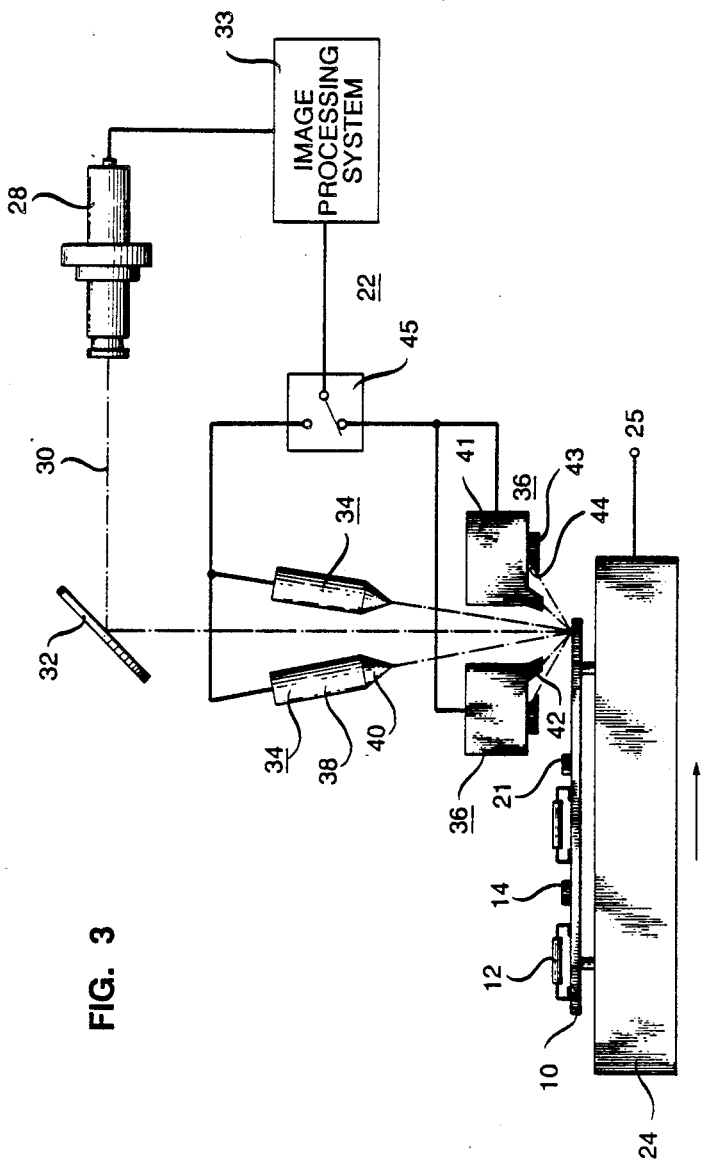
FIG. 3 is a schematic view of the circuit board inspection system of FIG. 1, depicting operation of the system in a second mode.

After the support 24 has been displaced along the axis 26 so that the circuit board 10 has been "scanned" by the camera 28, the image processor 34 actuates the switch 45 so that the pair of light sources 36 is rendered operative and the pair of light sources 34 is disabled. Referring now to FIG. 3, the support 24 is then displaced in the opposite direction along the axis 26, causing the circuit board 10 to be again scanned by the camera 28. The output signal of the camera 28 is processed in the manner described earlier so that only selected digital signals are stored, the stored signals representing the images of only the regions of interest on the circuit board 10 containing the leads 18 on the components 12). The stored digital signals are then processed to determine the location of the leads 18 from the fiducials 21. Then, the actual location of the leads 18 is compared to the expected lead location to determine if any of the components 12 are missing or misaligned.

Note that in the presently preferred embodiment the circuit board 10 is first illuminated with top light and thereafter is illuminated with side light. Alternatively, the circuit board 10 may be illuminated first with side light and then top light. However, it is more desirable to illuminate the board 10 with top light first so that the position of the fiducials 21 can be determined during the first pass of the circuit board by the camera 28.

The foregoing describes a technique for inspecting a circuit board to detect missing and misaligned active and passive components by scanning the circuit board twice while the board is illuminated with top and side light, respectively. The top light and side lighting of the circuit board enhance the features of the passive and active components, respectively, thus assuring more accurate inspection.

It is to be understood that the that the above-described embodiments are merely illustrative of the principles of the invention. Various modifications and changes may be made thereto by those skilled in the art which will embody the principles of the invention and fall within the spirit and scope thereof.

We claim:

1. A method of fabricating a substrate comprising the steps of:

placing at least one of a first type and at least one of a second type of component, having electrically conductive members, on a substrate so that each of the components has its conductive members in registration with corresponding metallized areas on the substrate;

adhering the first and second types of components to the substrate; and soldering the conductive members of the components to the substrate, characterized in that prior to the soldering step, the substrate is inspected to detect whether any of the first and second types of components are missing or misaligned, the inspection being accomplished by the steps of:

(a) illuminating the substrate with top light by directing light at the surface of the substrate so the light strikes the board substantially normal to the plane of the substrate surface to enhance the image of the conductive members of the first type of component;

(b) capturing, with a linescan camera, the image of a thin strip of area running across the surface of the substrate;

(c) imparting a relative motion between the substrate and the linescan camera so the camera captures the image of successive strips of surface area running across the board;

(d) storing the captured images for subsequent processing to determine if any of the first type of component are missing or misaligned;

(e) illuminating the substrate with side light by directing light at the substrate at a grazing angle wth respect to the surface to enhance the image of the conductive members on the second type of component;

(f) imparting a relative motion between the substrate and the linescan camera so the camera captures the image of successive strips of surface area running across the substrate; and (g) storing the captured images for subsequent processing to determine if any of the second type of component are missing or misaligned.

2. The method according to claim 1 wherein the stored images are processed by first determining the actual location of the conductive members on each component and then comparing the actual location to the expected location of the conductive members on the component.

3. A method of inspecting a substrate, which normally carries at least one of a first type and one of a second type of component, each having electrically conductive members, to detect whether any of the first or second types of components are missing or misaligned, comprising the steps of:

(a) illuminating the substrate with top light by directing light at the surface of the substrate so the light strikes the substrate substantially normal to the plane of its surface to enhance the image of the conductive members on the first type of component;

(b) capturing, with a linescan camera, the image of a thin strip of area running across the surface of the substrate;

(c) imparting a relative motion between the substrate and the linescan camera so the camera captures the image of successive strips of surface area running across the substrate;

(d) storing the captured images for subsequent processing to determine if any of the first type of component are missing or misaligned;

(e) illuminating the substrate with side light by directing light at the substrate at a grazing angle with respect to the plane of its surface to enhance the image of the conductive members on the second type of component;

(f) imparting a relative motion between the substrate and the linescan camera so the camera captures the image of successive strips of surface area running across the board; and (g) storing the captured images for subsequent processing to determine whether any of the second type of component are missing or misaligned.

4. The method according to claim 3 wherein the stored images are processed by first determining the actual location of the conductive members on each component and then comparing the actual location to the expected location of the conductive members on the component.

5. Apparatus for inspecting a substrate which normally carries at least one of a first and a second type of component, which each have conductive members in registration with metallized areas on the substrate surface, to determine if any of the first or second types of components are missing or misaligned, comprising:

a support, movable in opposite directions along a first axis for carrying the substrate;

a linescan camera positioned above the substrate for capturing the image of successive strips of surface area running along the surface of the substrate in a direction perpendicular to the first axis when the support moves along the first axis;

first means for directing light towards the substrate so the light strikes the surface of the substrate substantially normal to its plane to illuminate the substrate with top light in order to enhance the image of the conductive members on the first type of component;

second means for directing light towards the substrate so the light strikes the surface of the substrate at a grazing angle to illuminate the board with side light to enhance the image of the conductive members on the second type of component;

an image-processing system coupled to the linescan camera for storing and processing the images captured by the camera to detect if any of the first and second types of components are missing or misaligned; and means responsive to the image-processing means for selectively actuating a separate one of the light-directing means so that the substrate is sequentially illuminated with top and side light.

6. The apparatus according to claim 5 wherein the first light-directing means comprises a first pair of light sources located on opposite sides of the strip of surface area whose image is captured by the linescan camera, each first light source directing light at the surface of the board substantially normal to its plane to illuminate the strip of area whose image is captured by the linescan camera.

7. The apparatus according to claim 5, where the second light-directing means comprises a second pair of light sources located on opposite sides of the strip of surface area whose image is captured by the linescan camera, each second light source directing light at the surface of the board at a grazing angle to illuminate the strip of area whose image is captured by the camera.

* * * * *